United States Patent
Lindemans et al.

(10) Patent No.: US 6,748,653 B2
(45) Date of Patent: Jun. 15, 2004

(54) METHOD OF MAKING A TEMPORARY MEDICAL LEAD HAVING BIODEGRADABLE ELECTRODE MOUNTING PAD LOADED WITH THERAPEUTIC DRUG

(75) Inventors: Fredric W. Lindemans, Sittard (NL); Ursula Gebhardt, London (GB); Marc Hendriks, Brunssum (NL)

(73) Assignee: Medtronic, Inc., Minneapolis, MN (US)

( * ) Notice: Subject to any disclaimer, the term of this patent is extended or adjusted under 35 U.S.C. 154(b) by 84 days.

(21) Appl. No.: 09/947,433

(22) Filed: Sep. 7, 2001

(65) Prior Publication Data

US 2002/0035388 A1 Mar. 21, 2002

Related U.S. Application Data

(62) Division of application No. 09/411,837, filed on Oct. 4, 1999, now Pat. No. 6,385,491.

(51) Int. Cl.$^7$ ................................................ H05K 13/00
(52) U.S. Cl. .................... 29/854; 29/842; 29/857; 29/876; 424/428; 424/484; 600/375; 607/120; 607/130
(58) Field of Search .................. 29/842, 854, 857, 29/859, 868, 876, 592.1, 881, 883; 424/422, 423, 424, 425, 426, 428, 484; 600/374, 375; 607/116, 119, 120, 122, 129, 130, 131, 132

(56) References Cited

U.S. PATENT DOCUMENTS

| | | | |
|---|---|---|---|
| 4,765,341 A | * 8/1988 | Mower et al. | 607/116 |
| 4,913,903 A | 4/1990 | Sudmann et al. | 424/426 |
| 5,154,182 A | * 10/1992 | Moaddeb | 607/120 |
| 5,264,551 A | * 11/1993 | Petite et al. | 530/356 |
| 5,387,419 A | * 2/1995 | Levy et al. | 424/422 |
| 5,567,806 A | * 10/1996 | Abdul-Malak et al. | 530/356 |
| 5,618,563 A | * 4/1997 | Berde et al. | 424/501 |
| 5,660,854 A | * 8/1997 | Haynes et al. | 424/450 |
| 5,849,033 A | * 12/1998 | Mehmanesh et al. | 607/129 |
| 5,876,452 A | 3/1999 | Athanasiou et al. | 623/16 |
| 6,168,801 B1 | * 1/2001 | Heil et al. | 424/426 |

* cited by examiner

Primary Examiner—Peter Vo
Assistant Examiner—Donghai Nguyen
(74) Attorney, Agent, or Firm—Girma Wolde-Michael

(57) ABSTRACT

A method of making a temporary medical electrical lead for pacing or defibrillating a heart of a patient. The method comprises providing at least one electrical conductor having proximal and distal ends; providing an insulating sheath formed of biocompatible material extending over and covering at least portions of the at least one electrical conductor, attaching an electrical connector assembly to the proximal end of the at least one electrical conductor for attachment to a device capable of providing pacing or defibrillation pulses; providing an electrode mounting pad in the form of a cast matrix structure made of a biodegradable, biocompatible material soluble in human body fluids and having an outer heart non-contacting surface and an inner heart contacting surface, the outer surface being less permeable to passage of body fluids than the inner surface and wherein the inner surface of the pad has larger interstices and is less dense than the outer surface; providing a drug for treating for treating a medical condition of the patient's heart; loading the drug into the matrix of the pad; and attaching at least portions of the distal end of the at least one electrical conductor or of the electrode member to the electrode mounting pad.

15 Claims, 11 Drawing Sheets

METHOD OF MAKING A TEMPORARY MEDICAL LEAD HAVING BIODEGRADABLE ELECTRODE MOUNTING PAD LOADED WITH THERAPEUTIC DRUG

This is a divisional application of Ser. No. 09/411,837 filed on Oct. 4, 1999, now U.S. Pat. No. 6,385,491.

FIELD OF THE INVENTION

The present invention relates to the field of cardiac stimulation, and more specifically to the field of stimulating cardiac tissue using a medical electrical lead.

BACKGROUND OF THE INVENTION

Atrial arrhythmias and supra ventricular tachycardias, such as atrial fibrillation, atrial flutter and atrio-ventricular re-entry, are common post-operative complications among heart surgery patients. It is estimated that during the first seven to ten days after cardiac surgery post-operative supra ventricular tachycardia occurs in up to 63 percent of patients. Aranki et al. showed that patients with postoperative atrial fibrillation have a mean hospital stay of about fifteen days, whereas those patients without post-operative atrial fibrillation have a mean hospital stay of about ten days. Whether such extended hospitalization stays are primarily caused by arrhythmias is not known. See Cardiac Surg. Kirklin J W, Barrat-Boyes B C (Eds.): NY 1993, pg. 210, "The Importance of Age as a Predicator of Atrial Fibrillation and Flutter after Coronary Artery Bypass Grafting", Leitch et al., J. Thorac. Cardiovasc. Surg., 1990:100:338–42; "Atrial Activity During Cardioplegia and Postoperative Arrhythmias", Mullen et al., J. Thorac. Cardiovasc. Surg., 1987:94:558–65.

The presence of such arrhythmias, which in otherwise healthy patients may not be unduly serious, may be especially harmful to heart surgery patients. The surgery itself, the effects of prolonged anesthesia, or both have often already compromised the hemodynamic condition of such patients. Drugs that might be used to prevent post-operative atrial fibrillation are often only partially effective and may have negative effects on cardiac pump function.

Supra ventricular tachycardias may further cause a very irregular ventricular rate, which in turn can lead to hemodynamic conditions deteriorating even further. Such deterioration is especially serious for patients having a compromised left ventricular function. Such complications may also present a serious impediment to the recovery of the patient. See, for example, "Maintenance of Exercise Stroke Volume During Ventricular Versus Atrial Synchronous Pacing: Role of Contractility", Ausubel et al., Circ., 1985:72(5):1037–43; "Basic Physiological Studies on Cardiac Pacing with Special Reference to the Optimal Mode and Rate After Cardiac Surgery", Bailer et al., Thorac. Cardiovasc. Surg., 1981:29:168–73.

Due to the serious and potentially life threatening nature of the foregoing conditions, post-operative treatment is often aimed at preventing arrhythmias, such as through the use of drugs. Drugs, however, have been found not always to be effective at preventing arrhythmias. Thus, it is often necessary to provide a means for terminating any arrhythmias, which may occur. One common such means is over-pacing, more about which we say below.

If post-operative atrial fibrillation proves to have unacceptable hemodynamic consequences or causes serious symptoms, and if it does not stop spontaneously or antiarrhythmic drugs are ineffective in treating it, external cardioversion or atrial defibrillation may be required. But external atrial defibrillation, although generally effective as a treatment, may have profound side effects. First, and in contrast to ventricular defibrillation where conversion to normal sinus rhythm may occur after the first shock, atrial defibrillation may not be obtained until after several shocks have been delivered to the patient. This is because ventricular contraction continues during supra to ventricular tachycardia. Due to the large amounts of energy, which must be delivered in external defibrillation (e.g., 40 to 360 Joules), the shocks are not tolerated well by conscious patients. External defibrillation is therefore preferably performed under general anesthesia or at least when the patient is sedated. The use of anesthesia gives rise to yet another patient risk factor.

External defibrillation requires relatively high energy because the electrical source is not positioned directly upon the cardiac tissue and instead must pass through the thorax, which tends to dissipate the energy. In contrast, internally applied atrial defibrillation, such as may occur during surgery through defibrillation paddles placed directly on the heart, requires considerably less energy because the defibrillation electrical energy is applied only to the tissue that needs to be defibrillated. In fact, direct atrial defibrillation may be accomplished with only one-Joule pulses in contrast to the 40 Joule and greater pulses required for external defibrillation. See, for example, Kean D., NASPE abs. 246, PACE, April 1992, pt. II, pg. 570.

Defibrillation success rates generally depend on the amount of energy delivered. The lower amount of energy delivered, the lower the defibrillation success rate and the greater the number of shocks that must be applied to obtain successful defibrillation. By way of contrast, in direct atrial defibrillation, where energy is applied directly to the heart, the energy level can be selected such that the patient may more easily tolerate both the amount of energy delivered as well as the number of shocks required.

Waldo et al. in "Use of Temporarily Place Epicardial Atrial Wire Electrodes For The Diagnosis and Treatment of Cardiac Arrhythmias Following Open-Heart Surgery," J. Thorac. Cardiovasc. Surg., 1978, vol. 76, no. 4, pp. 558–65 disclose the use of a pair of temporary heart wires placed on the atrium to diagnose and treat arrhythmias through anti-tachycardia overdrive pacing. Specifically, temporary heart wires were sutured to the atrial walls at the time of the heart surgery. Once the patient was ready to be released from hospital, the wires were removed by traction or pulling upon the external end. See, for example, the temporary medical lead disclosed in U.S. Pat. No. 5,527,358 entitled "Temporary Medical Electrical Lead" to Mehmanesh et al., Temporary post-operative atrial and ventricular pacing with temporary heart wires has been found to successfully treat many post-operative arrhythmias. As such, the procedure has become widespread—at least 100,000 such procedures are performed each year. The procedure is not without problems, however, even where the most up-to-date heart wires are attached directly to the myocardium. As an example, temporary anti-tachy overdrive pacing is not always effective in terminating postoperative atrial arrhythmias or supra ventricular tachycardias. Improved temporary heart wires are thus required.

SUMMARY OF THE INVENTION

The present invention has certain objects. That is, various embodiments of the present invention provide solutions to one or more problems existing in the prior art respecting implantable pacing and/or defibrillation leads and conventional antiarrhythmic, pain-relieving or infection-inhibiting drugs, including one or more of: (a) patients experiencing post-operative arrhythmias and/or pain which may not be adequately treated through the use of temporary medical leads and defibrillatory electrical pulses only; (b) patients experiencing post-operative arrhythmias and/or pain which may not be adequately treated through the use of transvenously or orally delivered anti-arrhythmic or pain relieving drugs, and (c) patients developing post-operative implant-associated bacterial, viral or other infections of the heart.

Various embodiments of the present invention have certain advantages, including one or more of: (a) permitting lower defibrillation energy levels to be employed; (b) permitting fewer defibrillation pulses to be employed; (c) providing more efficient localized delivery of therapeutic or pain-relieving drugs to a patient's heart, and (d) providing quicker localized delivery of therapeutic or pain-relieving drugs to a patient's heart.

Various embodiments of the present invention have certain features, including one or more of: (a) a collagen or biodegradable electrode mounting pad loaded with one or more anti-arrhythmic drugs; (b) a collagen or biodegradable electrode mounting pad loaded with one or more pain-relieving drugs; (c) a collagen or biodegradable electrode mounting pad loaded with one or more antibiotic or antiviral drugs; (e) a method of making a drug-loaded collagen or biodegradable electrode mounting pad and associated electrode, and (f) a drug-loaded collagen or biodegradable electrode mounting pad which dissolves and disappears within a patient's body after a pre-determined post-operative period of time has elapsed which permits the electrical stimulating and drug delivery functions of the pad to have been performed.

BRIEF DESCRIPTION OF THE DRAWINGS

Other objects, advantages and features of the present invention will become apparent from the following specification, drawings and claims in which:

The drawings are not necessarily to scale. Like numbers refer to like parts or steps throughout the drawings.

DETAILED DESCRIPTION OF THE PREFERRED EMBODIMENTS

Figure 1:
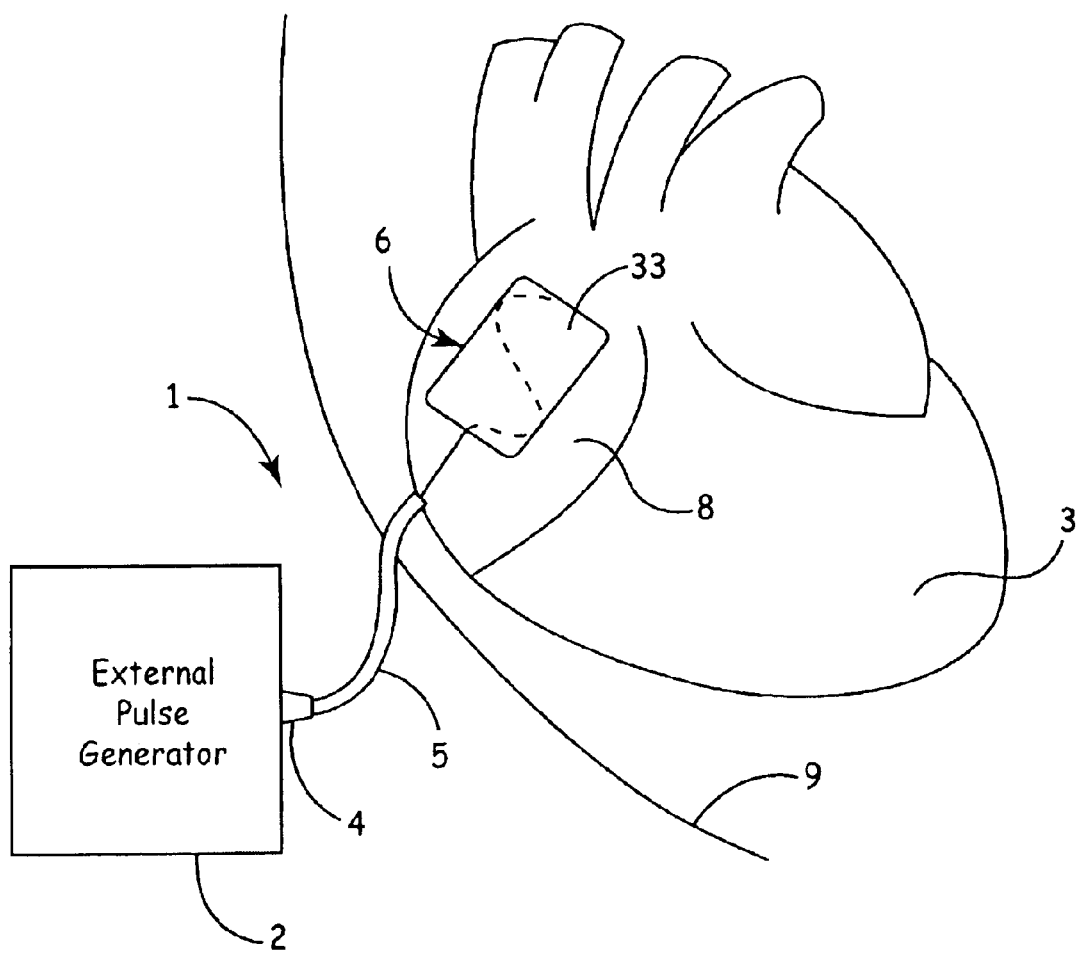
FIG. 1 shows a plan view of one embodiment of a lead of the present invention connected to an external pulse generator and a patient's heart.

FIG. 1 shows a plan view of one embodiment of lead 1 of the present invention. External pulse generator 2 is connected to patient's heart 3 by lead 1. Lead 1 comprises three sections: connector assembly 4, lead body 5 and electrode assembly 6. Typically two leads are attached to the heart: one to the left atrial wall and another to the right atrial wall. Defibrillation pulses are then delivered across the two electrodes through the left and right atria.

Connector assembly 4 connects lead 1 to external pulse generator 2, which may be, for example, an external pacemaker, external nerve or muscle stimulator, or an external defibrillator. Connector assembly 4 may be similar to any of several well known connector types disclosed in the prior art, such as the break-away needle connectors disclosed in U.S. Pat. No. 5,527,358, U.S. Pat. No. 5,871,528 and U.S. Pat. No. 5,792,217, all hereby incorporated by reference herein, each in its respective entirety. Connector assembly 4 may, for example, feature a break-away stainless steel needle having a recess which mates to a finger in a pin assembly. The break-away needle provided on the pin assembly permits the passage of connector assembly 4 from inside the body through the patient's skin to outside of the body. The break-away needle may thereafter be broken off at a breakpoint to permit the pin assembly to be connected to external pulse generator 2.

Alternatively, connector assembly 4 may comprise any of several types well known in the art suitable for electrically connecting the proximal end of lead 1 and the proximal end of electrical conductor 21 to implantable pulse generators (IPGs) such as implantable defibrillators, Implantable Pacer-Cardio-Defibrillators (PCDs), Implantable Cardio-Defibrillators (ICDs), implantable nerve stimulators, implantable muscle stimulators, implantable gastric system stimulators, and so on. That is, the lead of the present invention is not limited to use with external pulse generators only, but instead also finds application in conjunction with many types of implantable pulse generators.

Figure 2:
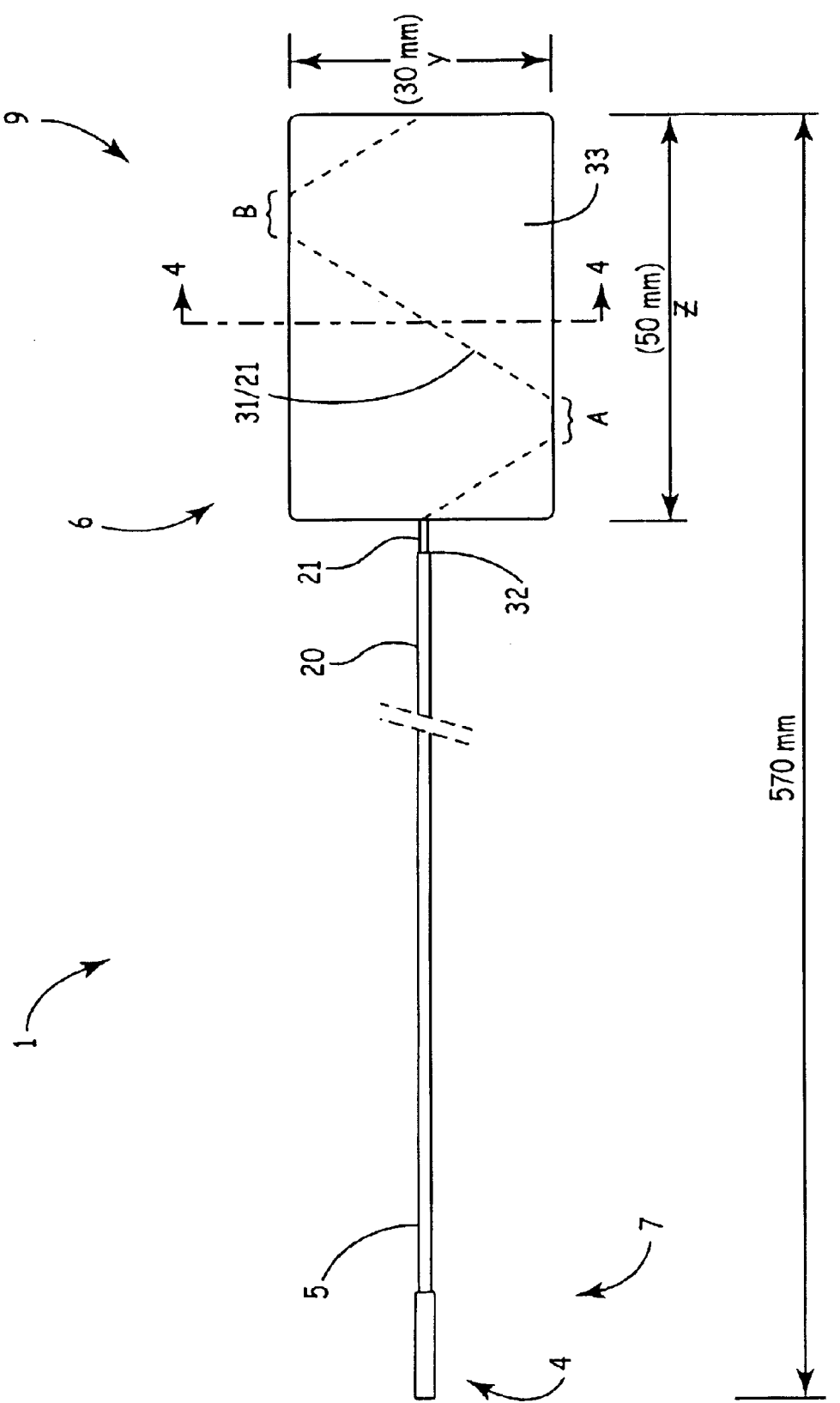
FIG. 2 shows a plan view of one embodiment of a lead of The present invention.

Referring now to FIG. 2, lead body 5 preferably comprises an insulative outer sleeve or sheath 20 having a central lumen, which encases one or more electrical conductors 21. Portions of the lumen forming unfilled gaps, such as gaps between one or more inner conductors 21, may be filled with medical adhesive. Outer sleeve 20 may be constructed from any suitable biocompatible (and preferably biostable) material such as FEP (fluorinated ethylene polymer), PTFE (polytetrafluoroethylene), PEBAX, TEFZEL, polyimide, PVDF (polyvinyldine fluoride), polyurethane, silicone rubber, or any other suitable material.

One or more inner conductors 21 are each constructed in a similar fashion. Thus, the construction of only one such conductor need be described. Inner conductor 21 preferably comprises a plurality of stranded wires, which form electrode wire 30. In a preferred embodiment of the present invention, inner conductor 21 is a multi-filament stainless steel stranded wire. It should be understood, of course, that any suitable material or wire may be employed to form conductor 21, including a coiled wire or any other type of wire made from an acceptable biocompatible material or metal including, but not limited to, such materials as platinum, palladium, titanium, tantalum, rhodium, iridium, carbon, vitreous carbon, and alloys, mixtures, combinations, oxides and/or nitrides of the foregoing. Of course, some materials are incompatible with others and may not be used effectively together. The limitations of specific electrically conductive materials for use with other electrically conductive materials in the context of implantation within the human body are well known in the art.

As best seen in FIG. 2, outer sleeve or insulation 20 terminates at location 32 near the distal end of lead 1. At least one electrical conductor 21 extends between proximal end 7 of lead 1 and distal end 9 of lead 1, and extends distally from the distal end of insulation 20 to terminate near or at distal end 9 of electrode assembly 6. Alternatively, a discrete electrode member may be crimped or otherwise attached to the distal end of at least one electrical conductor 21 and extend distally therefore for attachment to or positioning in or on electrode mounting pad 33. In either embodiment of the present invention, at least one electrical conductor 21 or the discrete electrode member forms an electrode or electrodes for providing electrical stimulation to a patient's heart tissue.

Although FIG. 2 shows only one electrical conductor attached to mounting pad 33, more than one such electrical conductor may be mounted or attached thereto. Note the semi-sinusoidal shape of the distal end of electrical conductor 21 in FIG. 2. Such a shape has been discovered to maximize the surface area of the heart that may be defibrillated by electrode 30 while still maintaining the ability of electrode 30 to be removed from pad 33 through the application of a non-excessive pulling force exerted upon the proximal end of lead 1 by a physician (more about which we say below).

Computer modeling and animal experiments confirmed the efficacy of the serpentine electrode configuration shown in FIGS. 1 and 2. Two acute animal experiments showed that the Defibrillation Thresholds (DFTs) obtained with a single wire serpentine electrode of the type shown in FIGS. 1 and 2 were equal to those obtained with a prior art temporary defibrillation lead having three wires or electrodes conforming generally to the lead disclosed in U.S. Pat. No. 5,527,358 discussed hereinabove. The single wire serpentine electrode of the present invention has the advantages of providing lower material costs, lower manufacturing costs, and being less invasive owing to the smaller diameter of the piercing needle, which it permits.

Figure 3:
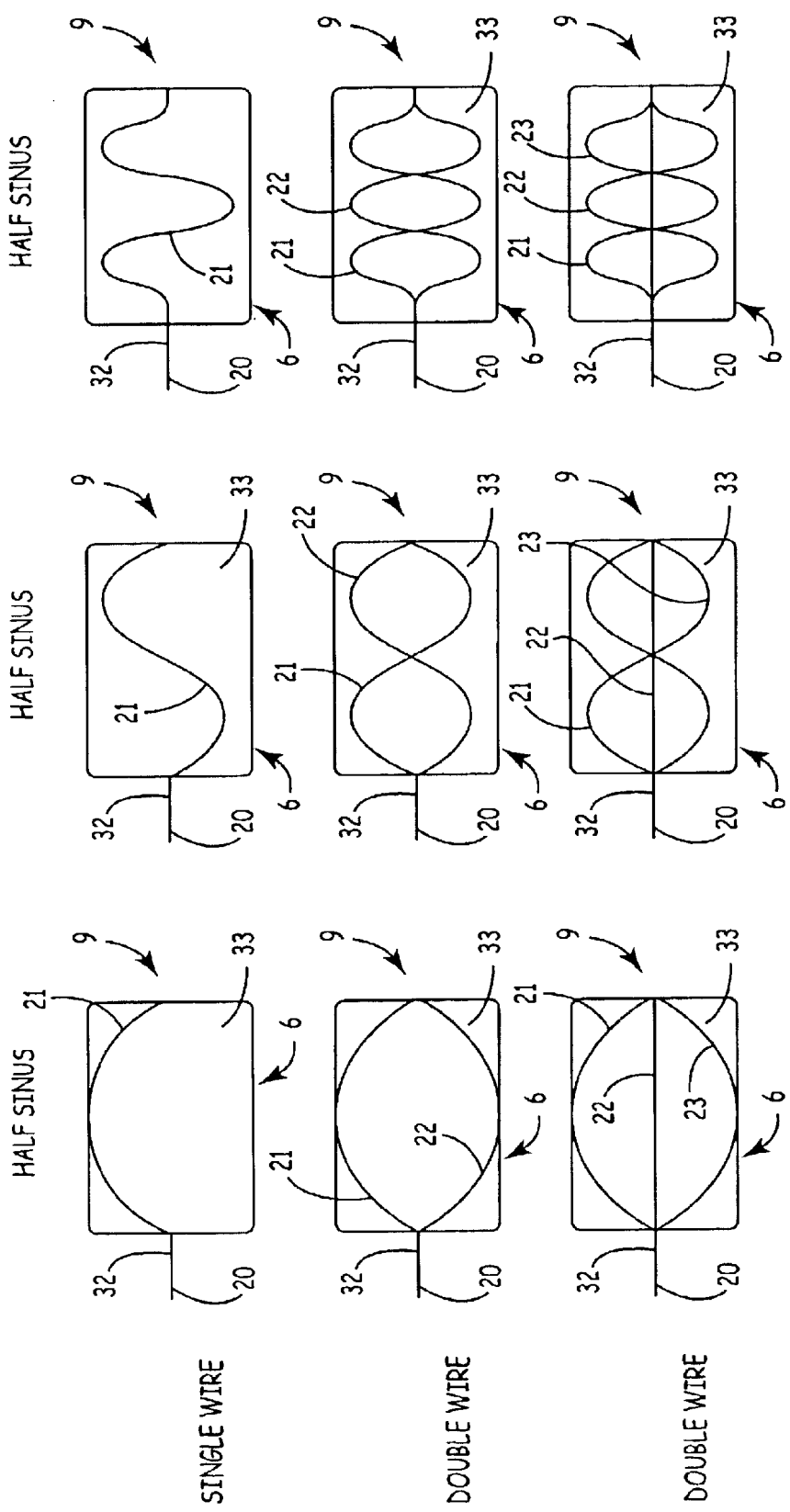
FIG. 3 shows plan views of various embodiments of the distal end of the lead of the present invention.

FIG. 3 shows several different embodiments of an electrode assembly that may be employed in conjunction with the present invention, including several embodiments where more than one electrical conductor or wire 21 is employed and attached to mounting pad 33. FIG. 3 shows electrical conductors 21, 22 and 23 arranged in various types of sinusoidal, curving or arcing configurations along mounting pad 33. It is to be noted, however, that the present invention is not limited in scope to embodiments having no more than three electrical conductors disposed on mounting pad 33, and specifically includes within its scope embodiments having more than three such electrical conductors. Additionally, the present invention is not limited in scope to embodiments where the one or more electrical conductors attached to mounting pad 33 assumes a sinusoidally-shaped, arced or curved configuration, but specifically includes within its scope embodiments having straight, triangular, rectangular, linear, non-curved, or non-arcing configurations. Electrode assembly 6 may assume any of several embodiments known in the art where more than one electrical conductor or wire 21 is employed and attached to mounting pad 33.

Figure 4:
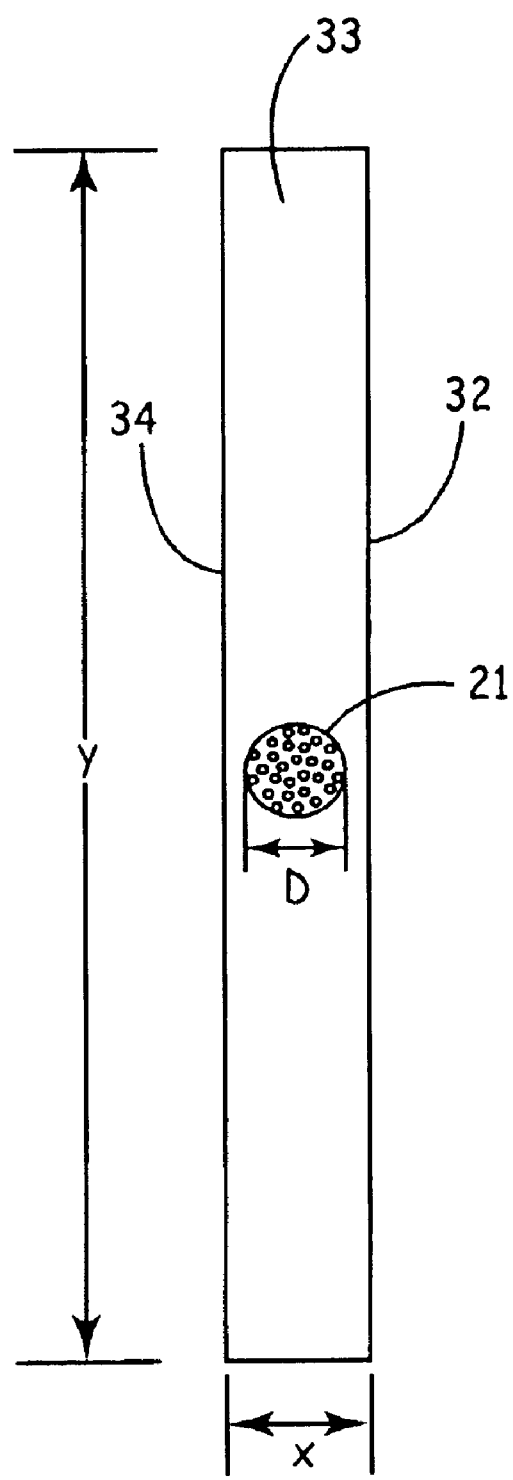
FIG. 4 shows a sectional view of the mounting pad and associated electrode of FIG. 2.

As noted above, electrode assembly 6 most preferably comprises one or more electrical conductors 21 and biocompatible, biostable mounting pad 33. The distal-most portion of each electrical conductor 21, 22 or 23 most preferably has a stranded metallic electrical conductor 30 exposed along the length of mounting pad 33. The distal end of electrical conductor 21 is most preferably disposed between opposing sides 32 and 34 of mounting pad 33, as shown in FIG. 4. In a preferred embodiment of the present invention, electrical conductor 21 is formed of about 49 individual medical grade stainless steel wires which are stranded together to form conductor 21 having a nominal diameter D of about 0.4 mm (see FIG. 3). In less preferred embodiments of the present invention, the wires may be braided or twisted together to form conductor 21.

Continuing to refer to FIGS. 2 and 4, thickness X of mounting pad 33 most preferably ranges between about 2 mm and about 3 mm, but may also range between about 1 mm and about 4 mm, or between about 0.5 mm and about 5 mm. Other thicknesses X and corresponding thickness ranges of mounting pad 33 are also contemplated in the present invention. Mounting pad length Z is most preferably about 50 mm, but may be any other suitable length. Likewise, mounting pad width Y is most preferably about 30 mm, but may be any other suitable width.

In the preferred embodiment of the present invention shown in the drawings hereof, one or more inner conductors 21 is shown mounted within mounting pad 33. It should be understood that such inner conductors may be mounted to mounting pad 33 in any acceptable manner including, without limitation, suturing or gluing all or some of inner conductor 21 to outer surfaces 32 or 34 of mounting pad 33. Holes may further be provided in mounting pad 33, either for the purpose of exposing certain portions of conductor 21 to heart tissue or reducing the mass of pad 33. Thus, when electrode assembly 6 is attached to cardiac tissue, intermittent sections of the one or more conductors are directly exposed to cardiac tissue through such holes. Mounting pad 33 may further feature suture areas or portions disposed near the corners of pad 33 which permit mounting pad 33 to be sutured directly to heart 3, as best seen in FIG. 1.

In one embodiment of the present invention, mounting pad 33 is constructed and formed from collagen, but may alternatively be fashioned from any suitable biodegradable, biostable, pliant material (more about which we say below). It is a particular advantage of the collagen embodiment of the mounting pad of the present invention that when mounting pad 33 is formed from an appropriate collagenous material, mounting pad 33 dissolves or otherwise dissociates over time following implantation within the human body. Consequently, even after electrode 30/inner conductor 21 is removed or explanted from a patient's body, mounting pad 33 remains implanted within the patient but then disappears over time as it dissolves in the human body fluids within which it is implanted. Mounting pad 33 is most preferably formed of a collagenous material that maintains its structural integrity long enough to permit the post-operative defibrillation function of lead 1 to be carried out. Once the electrode and lead have been explanted and removed from the patient (which typically occurs anywhere between one day to two weeks following the operation in which the lead was initially implanted), mounting pad 33 most preferably begins to dissolve and break down or otherwise dissociate, thereby losing its structural integrity.

Collagen is a natural biopolymer material well suited for use in forming the biodegradable, biocompatible, electrode mounting pad of the present invention. Collagen is the principal structural protein in mammals, constituting approximately one-third of the total body protein. As the chief structural protein of the body, collagen is capable of transmitting tensile and compressive forces of great magnitude. In light of the application of the present invention, such properties are highly desirable. After implantation, a collagen electrode mounting pad of the present invention is enzymatically degraded through the cleavage of peptide bonds by human collagenase. In a preferred embodiment of the present invention, the degradation rate of collagen is controlled by means of crosslinking. Crosslinking may also be employed to enhance the mechanical properties of the electrode mounting pad (more about which we say below), and furthermore beneficially diminishes the antigenicity of the electrode mounting pad.

Other biodegradable, biocompatible materials suitable for use in forming the electrode mounting pad of the present invention include natural materials and their corresponding synthetic equivalents or derivatives, such as albumin, silk, poly(L)lysin, fibrin, elastin, hyaluronic acid preparations, and salts and derivatives thereof such as those described in U.S. Pat. No. 5,128,326, glycos-amino-glycans, polysaccharrides, keratin, chondroitin sulfates, dermatan sulfate, keratan sulfate, heparan, heparan sulfate, heparan substitutes, heparin, heparin substitutes, cellulose and its derivatives, starch, gelatin, dextrans and their derivatives, chitin, chitosan, and combinations or mixtures of, or the products of reactions involving, the foregoing.

Still other natural and synthetic biodegradable, biocompatible materials suitable for use in forming the electrode mounting pad of the present invention include, but are not limited to, aliphatic polyesters, polyamides, polyesteramides, polyorthoesters, polyanhydrides, polyphosphazenes, Poly(glycolic acid), Poly(L-lactic acid), Poly(DL-lactic acid), Poly(p-dioxanone), Poly($\epsilon$-caprolactone), Poly(3-hydroxypropionic acid), Poly(3-hydroxybutyric acid), Poly($\alpha$-malic acid), Poly($\beta$-malic acid), Poly(serine ester).

Finally, it is fair to state that yet other natural and synthetic biodegradable, biocompatible materials, whether existing presently or in future, will find application and suitability in forming a biodegradable, biocompatible electrode mounting pad of the present invention.

An electrode mounting pad comprising collagen was constructed using collagen pads obtained from Coletica, a company based in Lyon, France. Those pads were similar to a hemostatic sponge marketed by Coletica in France, Spain and Italy under the mark "HEMOSTAGENE" and distributed in the U.S. by MedChem Products, Inc. under the marks "AVIFOAM" and "ACTIFOAM." Note that the pads provided by Coletica had been prepared by suspending collagen in an appropriate solution, pouring the suspension solution into a 6 cm×6 cm metal cast, freezing and freeze-drying the solution contained within the cast, and pressing the resulting freeze-dried sponge to a thickness of 3 mm between plates heated to 80 degrees Celsius for 30 seconds at a pressure of 180 bars. Thereafter the pads were cut to appropriate size.

Figure 5:
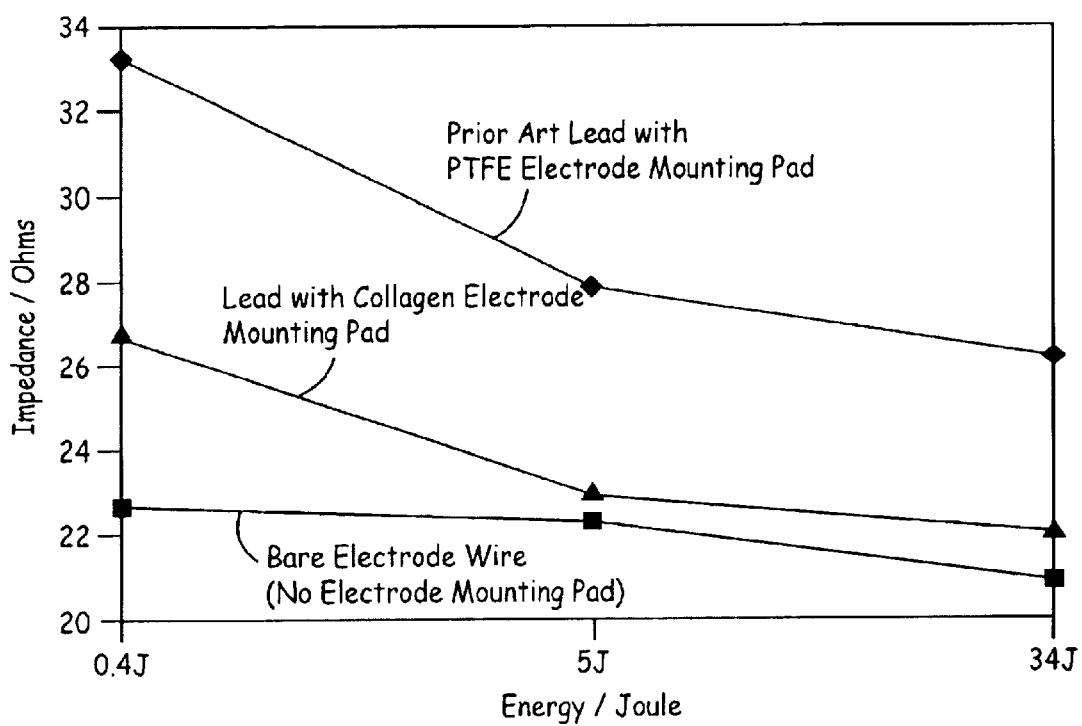
FIG. 5 shows comparative impedance versus energy data for a lead of the present invention and two prior art leads.

In a pre-clinical experiment, impedance measurements were performed to determine the conductivity of the collagen pad. Three different devices were compared: (1) Medtronic Model No. 13004 lead with PTFE electrode mounting pad; (2) Medtronic Model No. 13004 lead with bare wires and no electrode pad, and (3) Medtronic Model 13004 lead with collagen electrode mounting pad. The tested electrodes were positioned in a water bath containing a 0.9% saline solution at room temperature. Electrical shocks were applied between the test electrodes and a Medtronic Model No. 6721M epicardial patch electrode. The distance between the electrodes was set at 49 cm. For the delivery of the electrical shocks a Medtronic DISD Model No. 5358 and a Medtronic Model No. 9790 programmer were employed. Three experimental runs were performed for each tested device. The results of the tests are depicted in FIG. 5. After three hours the tests with the collagen pad were repeated; no significant differences were observed in comparison to the first test results obtained (indicating that the collagen pad was essentially instantaneously hydrated).

FIG. 5 shows that a device having the collagen electrode mounting pad of the present invention has a lower impedance than a device containing a PTFE electrode mounting pad, and further exhibits impedance characteristics comparable to those of a bare electrode wire. In other words, the collagen electrode mounting pad of the present invention provides low lead system impedance, which is a highly desirable feature in a temporary atrial or ventricular defibrillation lead.

After obtaining the foregoing results, several acute implants in sheep were performed to test the feasibility of the new concept in vivo. The study's objective was to determine the DFTs of a lead made according to the present invention, and to determine whether the collagen electrode pad of the present invention was capable of preventing electrical damage to the atrial wall. In a small experiment involving only two implants in sheep, a mean DFT of 120 Volts (i.e., 0.8 Joules) was measured. No acute damage to the atrial walls was observed after shocking 10 times at 288 Volts (i.e., 5 Joules). Fixation of the electrode mounting pad onto the atrial walls was observed to be good. However, immediately after implantation the collagen pads demonstrated major shrinkage with reductions in length and width of about 50%, thereby causing partial exposure of the bare wire electrodes. Such a loss in dimensional integrity was not acceptable, and the underlying cause of the shrinkage was investigated by means of calorimetry to provide detailed information on the heat stability of the collagen material employed to form the electrode mounting pads.

When collagen is heated in a hydrated state it denatures at a specific temperature, resulting in shrinkage of the material. This shrinkage occurs as a result of the macroscopic manifestation of the transformation of collagen's native triple-helix structure to a random coil configuration. Differential scanning calorimetry (DSC) is frequently used to determine the denaturation temperature of collagen materials. DSC determines the difference in energy necessary to keep a sample pan and a reference pan at the same temperature.

The collagen obtained from Coletica to form the electrode mounting pads of the present invention was characterized using a Perkin Elmer DSC. A 5–10 mg collagen sample was placed on a 50 ml aluminum DSC sample pan having a 2 bar maximum internal pressure, after which 5 ml/mg 0.1M phosphate buffer (pH=6.88; 0.05M $Na_2HPO_4$, 0.05M $NaH_2PO_4$) was added to hydrate the collagen. The sample pan was covered with an appropriate cover and the whole was crimp pressed. An empty sample pan was used as the reference. Typically, a run was started at 20° C. (load temperature); after 2 minutes, samples were heated to 80° C., applying a heating rate of 2° C./min. Device software was used to optimize data collection, and to calculate typical properties.

Figure 6:
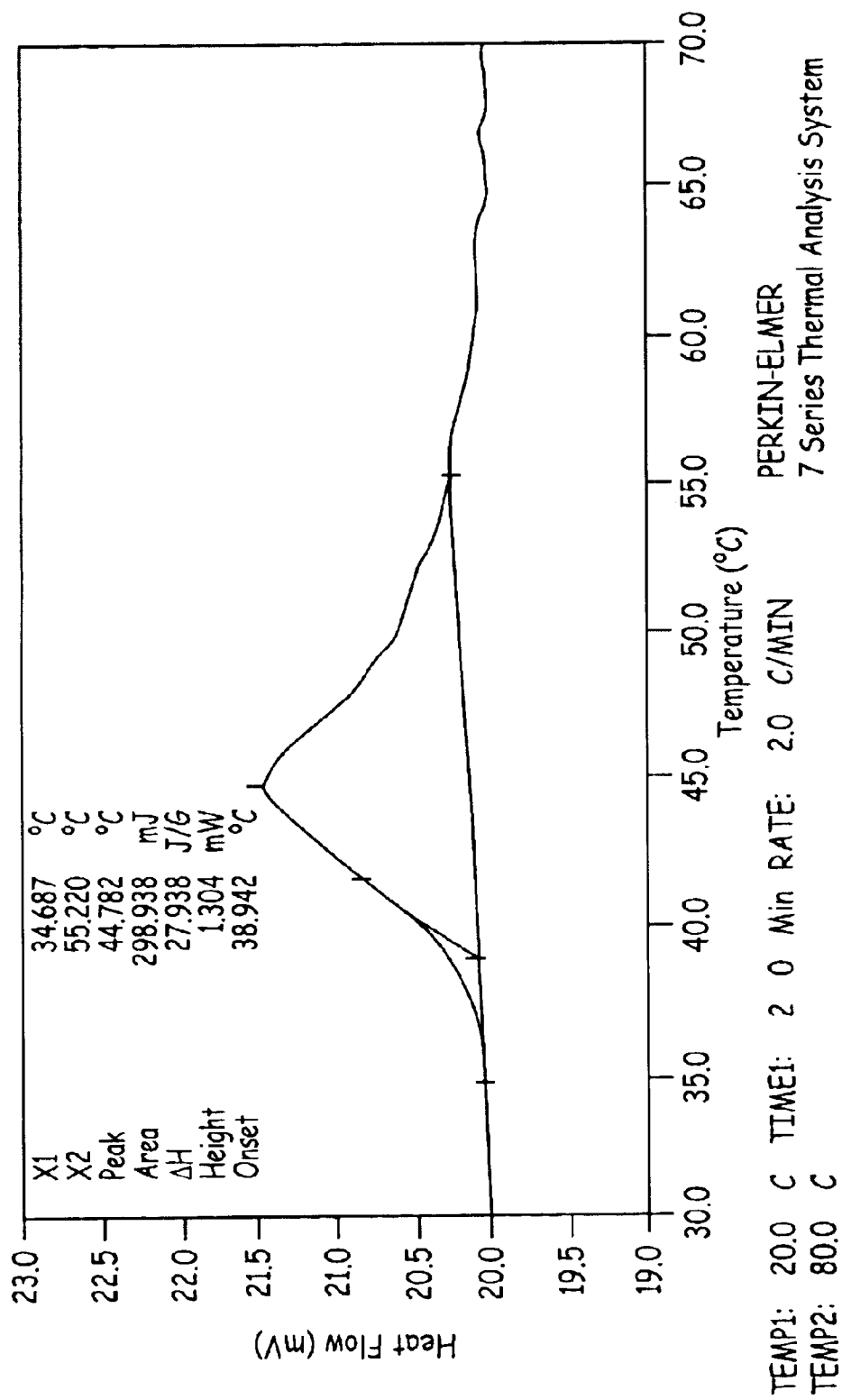
FIG. 6 shows the results of calorimetric analysis of one type of collagen material finding application in the present invention.

The resulting thermogram of FIG. 6 shows a wide peak with significant tailing. Such tailing denotes the heterogeneous character of the tested material, since short triple-helical segments more easily unwrap (or denature) than do long triple-helical segments.

Few processes exist that are suitable for sterilizing collagen products. Moist heat (or autoclaving) cannot be used to sterilize collagen because the hydrated protein is susceptible to thermal denaturation. Gaseous ethylene oxide (ETO) sterilization may be employed to sterilize collagen under moistened conditions, elevated temperatures and pressures. If the temperatures employed in ETO sterilization are not excessive, little helical denaturation occurs. Ethylene oxide reacts with the collagen. Losses of the amino acids lysine and hydroxylysine, in particular, suggest that free amino groups participate in the reaction with ethylene oxide. There is little doubt that such reactions may affect the physical and biological properties of the collagen. Consistency in the treatment and sterilization of collagen materials is therefore important.

E-beam or alpha-irradiation may also be employed to sterilize collagen products. It has, however, been shown conclusively that such methods of sterilizing collagen have a significant impact on the stability of collagen. Depending on the particular product application, therefore, irradiation/sterilization of collagen may not be appropriate.

DSC techniques were next employed to determine the relative efficacies of the three foregoing sterilization methods (i.e., ETO, E-beam and alpha-irradiation sterilization). The results obtained are shown in Table 1 below, where it becomes obvious that sterilization per se lowers the denaturation temperature of collagen material. All temperatures shown in Table 1 are in Degrees Celsius.

TABLE 1

Effect of Sterilization on Heat Stability of Collagen

| Type of Material | Peak Start Temp. | Peak End Temp. | Peak Temp. | Onset Temp.* |
|---|---|---|---|---|
| Control (non sterilized) | 36.4 | 59.9 | 44.2 | 39.6 |
| Gamma sterilized | 28.3 | 52.1 | 38.7 | 33.0 |
| E-beam sterilized | 31.3 | 50.0 | 39.4 | 35.4 |
| ETO sterilized | 35.0 | 57.1 | 40.9 | 37.2 |

*onset temperature is the temperature at which the tangent in the inflection point crosses the baseline.

As Table 1 shows, and in comparison to the control material, ETO sterilization was observed not to change the heterogeneity of the collagen material, whereas both E-beam and alpha-irradiation seem to decrease the heterogeneous character of collagen material (by exhibiting less DSC tailing). The foregoing observations in combination with the lowering of the peak start temperatures confirm that chain-scission occurs in collagen molecules, whereby shorter triple helix segments are introduced into the collagen fibers. Those shorter segments unwrap more easily during heating.

As discussed above, ETO sterilization chemically modifies collagen. The chemical modification resulting from ETO sterilization may reduce the stability of triple helix segments such that collagen denaturation is facilitated. The thermogram of FIG. 6 shows that denaturation of ETO sterilized collagen begins at a temperature, which is below the normal body temperature of a human subject. Our calorimetric data thus help explain the findings of the first acute implant study, in which the collagen pad demonstrated major shrinkage upon contact with the atrial wall. Thus, ETO sterilization of collagen is the most preferred of the three investigated sterilization methods.

Table 2 below shows results obtained using a crosslinked collagen material, where all temperatures are in Degrees Celsius. Table 2 shows that crosslinking of collagen increases its denaturation temperature. Collagen's triple helix structure is stabilized by hydrogen bonds, which are heat unstable. Introduction of covalent crosslinks increases the stability of the triple helix, and thus increases the denaturation temperature. In the present invention, physical or chemical crosslinking methods may be employed to crosslink collagen-based materials. In addition to the increase in denaturation temperature, crosslinking also enhances the resistance to biodegradation of the material, suppresses its antigenicity and improves its mechanical properties.

As discussed above, major shrinkage of non-crosslinked collagen electrode mounting pads was observed to occur after the pads were positioned in vivo on the atrial wall. Such losses in dimensional integrity were deemed unacceptable. Crosslinking with a water-soluble carbodiimide was thus performed as a means to increase the denaturation temperature and enhance the in vivo stability of the collagen electrode mounting pad. The method of carbodiimide crosslinking was selected for its ease of operation and because carbodiimide crosslinked collagen materials generally demonstrate suitable biocompatibility properties. Our objective was to achieve an onset of the denaturation temperature slightly above body temperature between about 40° C. and about 45° C. Crosslinking specifications were set to limit the impact crosslinking would have on the biodegradation characteristics of the collagen material.

Next, calorimetry techniques were employed to permit optimization of the crosslink process. After the collagen material was exposed to various concentrations of selected crosslinking reagents, the consequent change in denaturation temperature was determined (see Table 2 below). Crosslinked materials were also ETO sterilized to determine and take into account the decrease in denaturation temperature ETO sterilization causes.

In the crosslinking process employed to acquire the data shown in Table 2 below, a collagen pad measuring about 50×30 mm and having a mass of about 0.5 grams was first hydrated in a PP beaker holding 50 ml of a 0.25M MES buffer solution (adjusted to pH=5.0 by dropwise addition of 1N NaOH). After 30 minutes the collagen pad was withdrawn from the solution and carefully positioned on lint-free towels to permit excess buffer solution to drain away. Next, 50 ml of a 0.25M MES buffered solution (pH=5.0) containing crosslinking reagents EDC (3-ethyl-1-(diaminopropyl) carbodiimide HCl) and NHS (N-hydroxy succinimide) prepared, and within 5 minutes after adding EDC and NHS to the buffered solution the collagen pad was immersed therein. Crosslinking was permitted to proceed for 2 hours while gently shaking the buffered solution. Following crosslinking, the electrode mounting pad was first washed in distilled water three times for 15 minutes, then rinsed washed in a solution containing 0.1M $NaH_2PO_4$ for 2 hours, and then rinsed three times in distilled water for 15 minutes. Finally, the crosslinked collagen electrode mounting pad had excess water drained therefrom and was placed in a freezer at a temperature below −70° C. Once completely frozen, the collagen pad was freeze dried overnight.

TABLE 2

Effect of Crosslinking on the Heat Stability of Collagen

| Sample | Crosslinking Level EDC [μM] | NHS [μM] | Peak Start Temp. | Peak End Temp. | Peak Temp. | Onset Temp. |
|---|---|---|---|---|---|---|
| A | 60000 | 24000 | 66.2 | 82.2 | 77.7 | 68.4 |
| B | 12000 | 12000 | 53.8 | 74.2 | 65.8 | 60.5 |
| C | 6000 | 6000 | 57.4 | 67.9 | 64.0 | 60.6 |
| D | 3000 | 3000 | 56.6 | 65.4 | 61.4 | 58.7 |
| E | 1000 | 1000 | 49.2 | 65.2 | 54.7 | 50.3 |
| F | 100 | 100 | 39.9 | 65.9 | 49.9 | 44.3 |
| G | 10 | 10 | 38.6 | 65.2 | 47.6 | 42.8 |
| Control | 0 | 0 | 36.4 | 59.9 | 44.2 | 39.6 |

Figure 7:
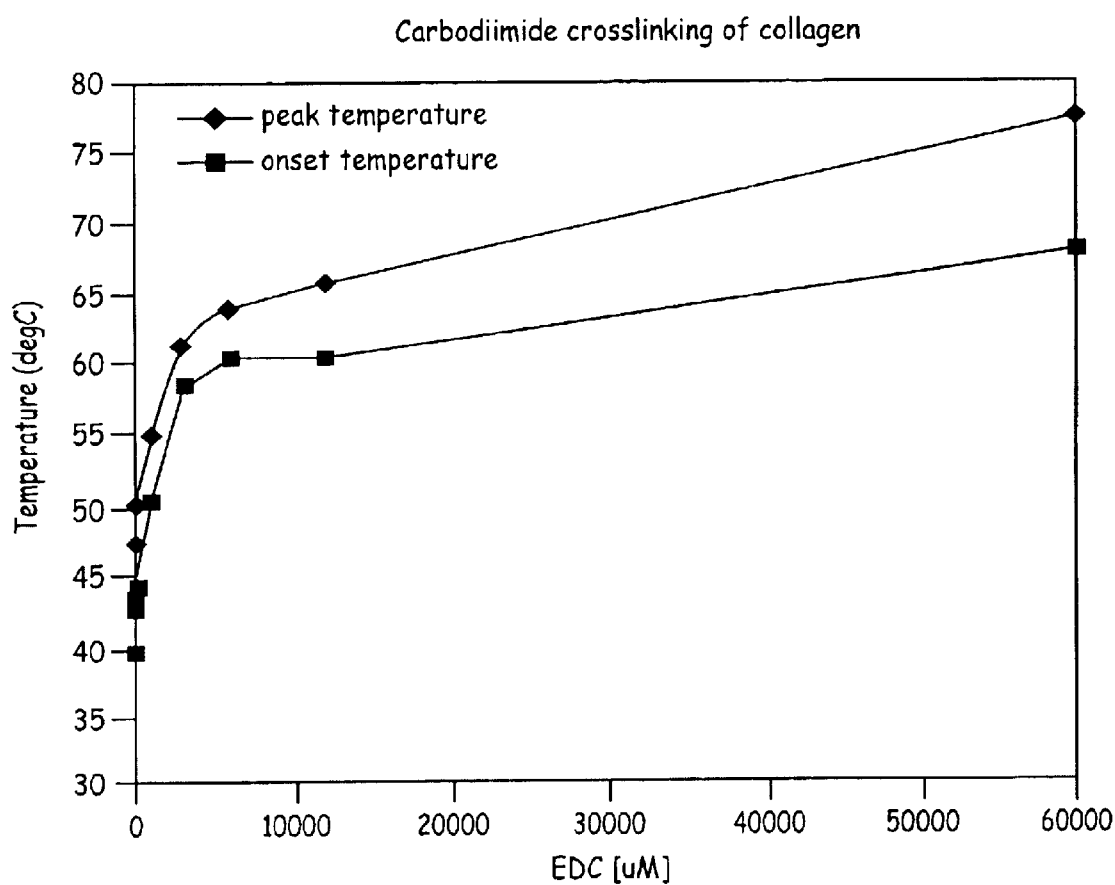
FIG. 7 shows the increase in the onset of the denaturation temperature, which occurs in a crosslinked collagen material of the present invention.

Data corresponding to Table 2 above are shown in FIG. 7, where it is shown that an immediate increase in the onset of the denaturation temperature occurs in crosslinked collagen materials of the present invention, even at low reagent concentrations. As discussed above, an increase in denaturation temperature is directly related to enhanced resistance of biodegradation. Thus, an initial temperature ranging between about 43° C. and about 45° C. at which denaturation begins to occur was determined to provide satisfactory results in at least some embodiments of the present invention. In the light of such considerations, further experiments were conducted using collagen materials made according to the conditions and specifications corresponding to Sample F in Table 2. Materials conforming to the conditions and specifications of Sample F were chosen over those corresponding to Sample G because ETO sterilization lowers the temperature at which the onset of denaturation occurs.

Next, the effects of ETO sterilization on crosslinked collagen electrode mounting pads was determined by calorimetric means. Table 3 below shows the results obtained, where all temperatures are in Degrees Celsius.

TABLE 3

Effect of Sterilization on Heat Stability of Collagen

| Type of Material | Peak Start Temp. | Peak End Temp. | Peak Temp. | Onset Temp. |
|---|---|---|---|---|
| Crosslinked F (non sterilized) | 39.4 | 61.7 | 49.2 | 43.7 |
| Crosslinked F (ETO sterilized) | 38.6 | 61.7 | 48.3 | 41.6 |

In combination with the results shown in Table 2 above, Table 3 shows that crosslinking collagen electrode mounting pads using the conditions and specifications corresponding to sample F results in collagen denaturation temperatures which prevent or at the very least substantially impede in vivo shrinkage of the electrode mounting pad of the present invention.

Next we determined by in vitro collagen digestion means whether the crosslinked collagen material of the present invention made according to the optimum crosslinking techniques and parameters described above affected enzyme degradation profiles significantly in respect of non-crosslinked control collagen materials. To that end we obtained enzyme degradation profiles for non-crosslinked control collagen materials as well as for collagen materials made according to the specifications and processes corresponding to crosslinked collagen Sample F described above.

Our experimental procedures for in vitro collagen digestion were as follows. First, the weight of individual collagen strips was recorded. A collagenase stock solution was prepared, after which 5 ml aliquots were immediately frozen at a temperature below −18° C. The collagenase stock solution was a 0.1 M Tris-HCl (Sigma Chemie, Bornem, Belgium) buffered solution having a pH of 7.4, containing 5 mM $CaCl_2$ (Acros Chimica, Geel, Belgium), 0.05 mg/ml $NaN_3$ (Merck-Schuchardt, Darmstadt, Germany), and 10 U/ml collagenase (EC 3.4.24.3; from Clostridium histolyticum; type IA, 550 units/mg solid; Sigma Chemie, Bornem, Belgium). Prior to use the aliquots were thawed. Collagen strips (n=3; approx. 0.05 g) were subjected to collagenase digestion by immersion of the individual strips in 5 ml of collagenase solution at 37° C. (collagenase:collagen=1 U/mg). After 1 hour, collagenase digestion was terminated by adding 0.5 ml of 0.25 M EDTA (99%; Acros Chimica, Geel, Belgium). Thereafter, the strips were rinsed three times for 5 minutes in 0.1 M Tris-HCl having a pH of 7.4, after which the strips were rinsed a further three times for 5 minutes in distilled water. Finally, the strips were frozen for 2 hours at about −80° C. and freeze dried overnight. Thereafter, the weight of each strip was determined and the weight loss of each recorded. Digestion was continued as above until complete dissolution of the collagen strips occurred.

Figure 8:
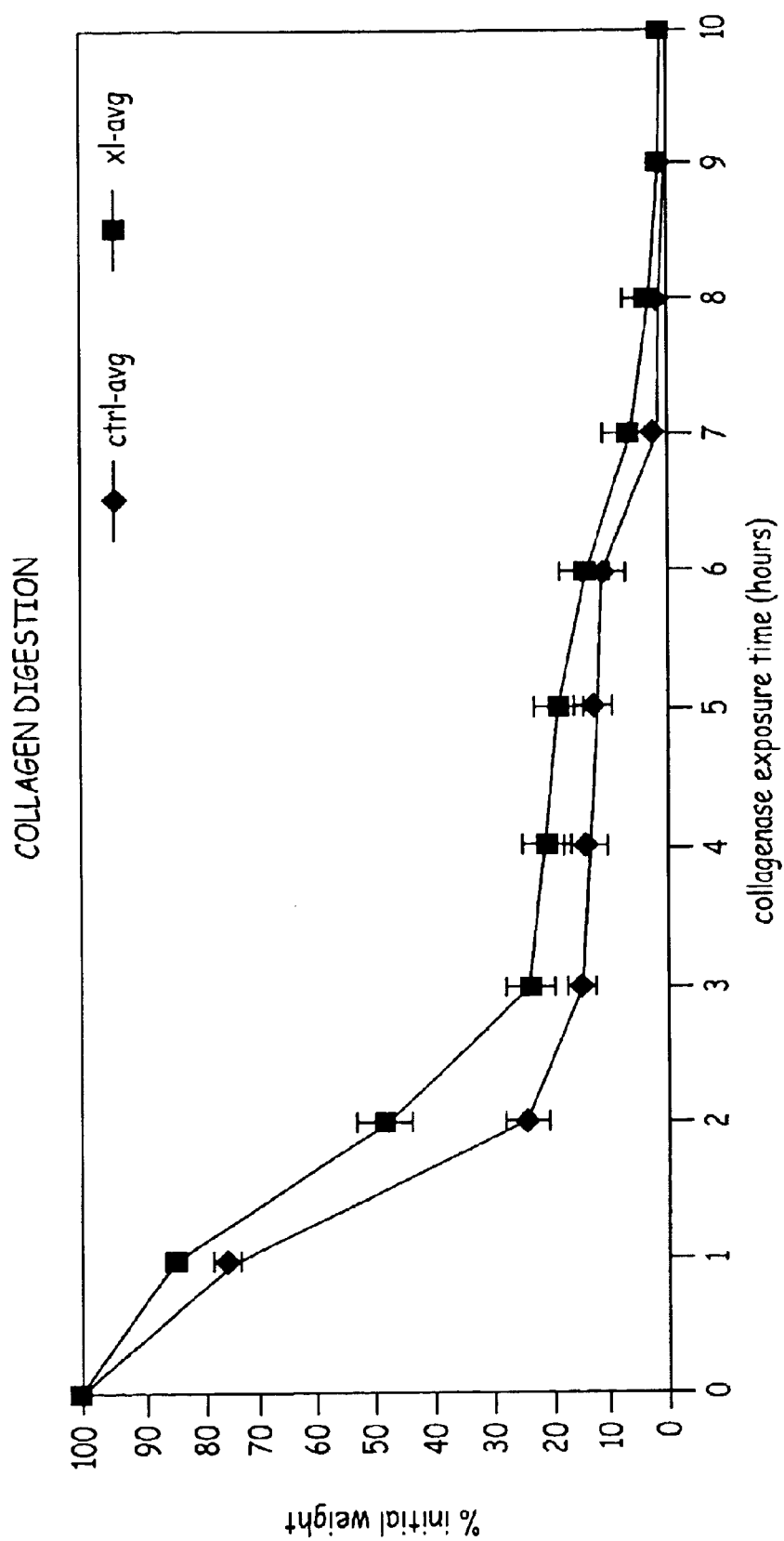
FIG. 8 shows comparative digestion profiles for crosslinked and non-crosslinked collagen materials.

FIG. 8 shows the degradation profiles obtained for the control (i.e., non-crosslinked) collagen samples and the crosslinked collagen samples made according to the conditions and specifications of Sample F. FIG. 7 shows that crosslinked collagen samples of the present invention take slightly longer to degrade than do non-crosslinked collagen samples. The increase in the amount of degradation time is very slight, however. Such a slight increase in degradation time is consistent with our initial objective of introducing a level of crosslinking in collagen, which did not appreciably affect the biodegradation characteristics of the collagen.

Another observed feature of crosslinked collagen samples in comparison to non-crosslinked samples was that degradation seemed to be changed into a surface erosion process in the crosslinked samples (as opposed to the bulk erosion processes noted in non-crosslinked samples). Unlike the early fragmentation observed in the non-crosslinked control samples, the crosslinked samples maintained their original shapes almost until the end of each experiment. Such degradation characteristics of crosslinked collagen materials may be highly advantageous in respect of maintaining the dimensional integrity of a collagen pad during the functional lifetime of an implanted temporary defibrillation lead.

In accordance with the foregoing observations and teachings, collagen electrode mounting pads appear to be much more suitable for use in temporary implantable defibrillation leads than do prior art PTFE felt electrode mounting pads. One chief advantage of the collagen electrode mounting pad of the present invention is the fact that a collagen pad is resorbed into the body over time so that eventually no foreign material remains in the body. Moreover, varying the degree or amount of crosslinking, which is permitted to occur in the collagen may be employed as a technique for controlling the rate at which degradation of the electrode mounting pad of the present invention proceeds when implanted within the human body.

Yet another advantage of the collagen electrode mounting pad of the present invention is the demonstrated improvement in increased conductivity (or lowered impedance) obtained with a collagen electrode mounting pad in respect of a PTFE felt electrode mounting pad. Moreover, although the conductivity of the collagen electrode mounting pad is similar to that of a bare wire, one preferred embodiment of the collagen electrode pad of the present invention helps to minimize tissue damage since the atrial wall is not permitted to directly come into contact with the defibrillation electrode (which is disposed within a matrix of surrounding collagen—see FIG. 4).

Figure 9:
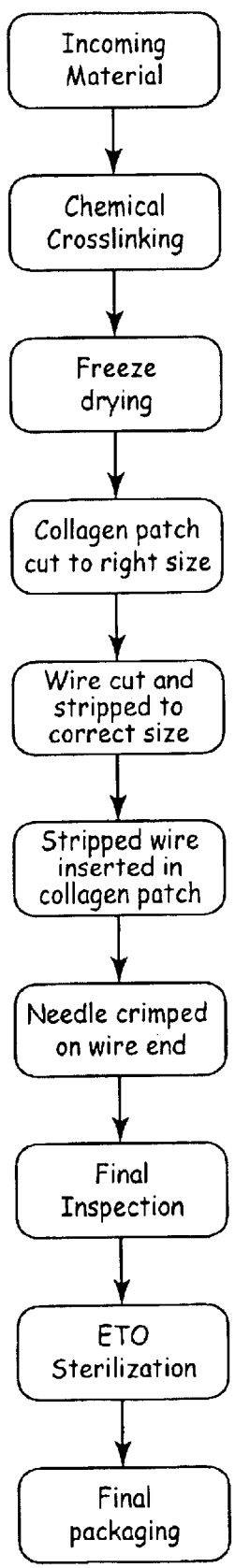
FIG. 9 illustrates one method of making a lead of the present invention.

FIG. 9 shows one method of the present invention for making a temporary defibrillation lead. After the collagen electrode mounting pad has been crosslinked, freeze dried, and cut to the proper dimensions, electrode wire/conductor 30/21 is most preferably woven through the collagen matrix using a needle. After electrode wire 30/conductor 21 has been appropriately placed in electrode mounting pad 33, break-away connector assembly 4 and its corresponding piercing needle are crimped to proximal end 4 of the lead body.

Referring now to FIG. 2, when electrode wire 30/at least one electrical conductor 21 is threaded by needle means through the collagen matrix of electrode mounting pad 33, collagen/electrode mounting pad 33 is sliced in regions A and B to permit electrode wire/conductor 21 to be re-inserted by hand into the collagen matrix in a different direction or orientation.

In another embodiment and method of the present invention, electrode wire 30/at least one electrical conductor 21 is appropriately placed and oriented in an electrode mounting cast, and a collagen-containing solution is poured therein which at least partially, if not entirely, surrounds or encases electrode wire 30/at least one electrical conductor 21. After being subjected to suitable crosslinking, dehydration and/or freeze drying processes, the collagen electrode mounting pad containing electrode 30/conductor 21 is removed from the cast and the lead is subjected to any further processing which may be required.

Figure 10:
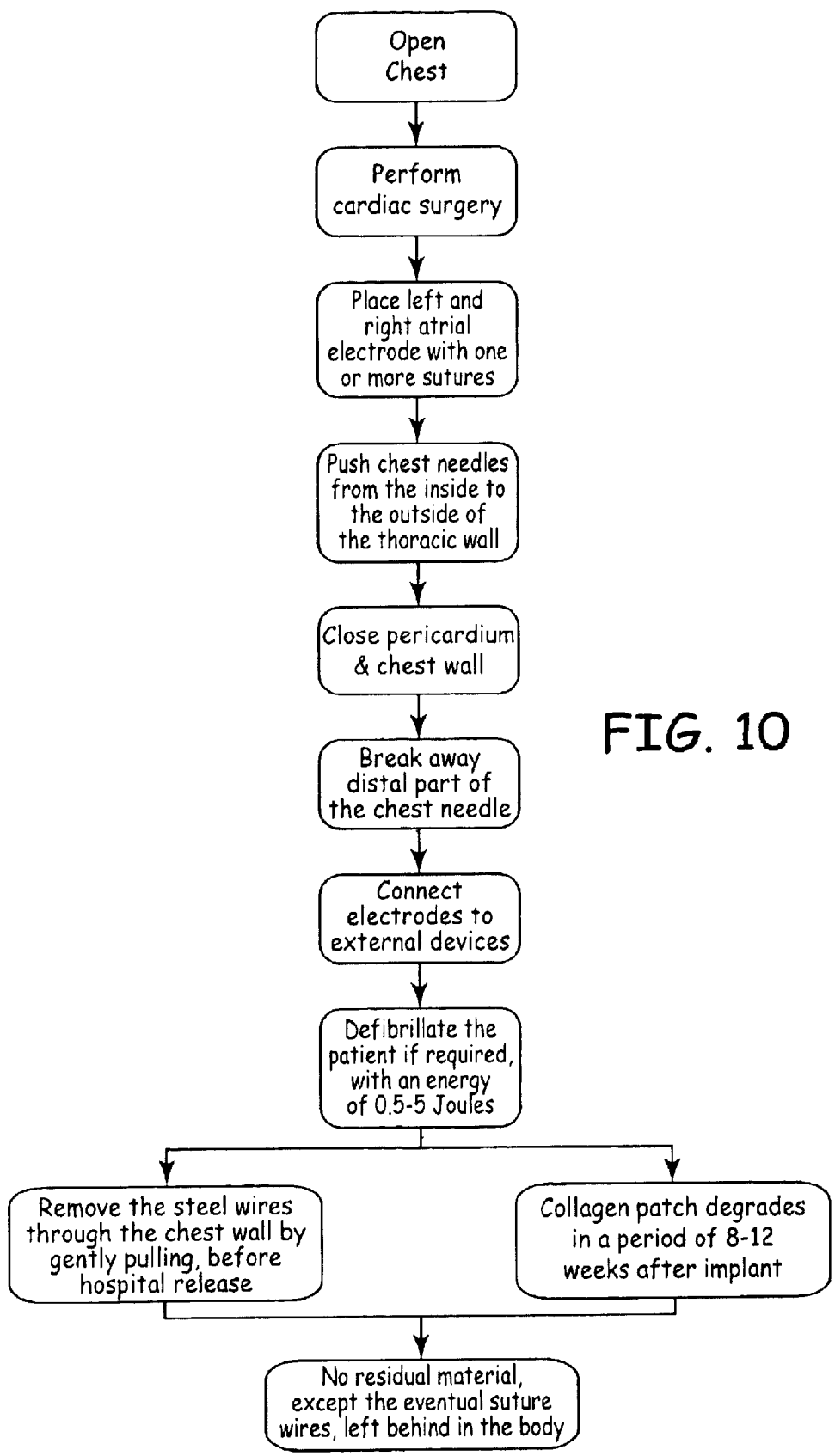
FIG. 10 illustrates one method of implanting and removing a lead of the present invention.

Referring now to FIGS. 1 and 10, in one method of the present invention implantation of lead 1 proceeds as follows. Electrode mounting pad 33 is sutured to atrium 8 using suture areas 35. Next, connector assembly 4 is exteriorized at a point away from the incision through the use of a break-away needle and pin assembly known in the art (see, for example, U.S. Pat. No. 5,527,358 entitled "Temporary Medical Electrical Lead" to Mehmanesh et al.). The needle is used to pierce the skin from the interior to the exterior so as to the pin assembly. Once lead 1 is satisfactorily sutured to the atrium, the pin assembly is exposed and the lead is connected to external pulse generator 2. The incision in the patient may then be closed. At this point lead 1 can deliver therapeutic electrical pulses, including defibrillating, cardio-verting or pacing pulses, to atrium 8. Note that in the present invention an implantable pulse generator may be substituted for external pulse generator 2.

One important aspect of one embodiment of the lead of the present invention is the ease with which it may be removed from a patient within which it has been implanted. Conductor 21/electrode 30 is mounted within mounting pad 33 so that it may be removed, even once implanted, through the application of tractional or gentle pulling forces. That is, the distal end of conductor 21 affixed to mounting pad 33 may be gently removed therefrom through the application of a tractional force upon proximal end 5 of lead 1. Alternatively, and depending upon various factors such as the amount of time mounting pad 33 has been implanted within the patient and the degree of crosslinking which has been permitted to occur in mounting pad 33 during the manufacturing process, removal of conductor 21 from the patient may require the application of little tractional force owing to electrode pad 33 having been resorbed or dissolved in the patient's body by the time conductor 21 is pulled from the patient's body.

We turn now to important aspects of the present invention concerning drug loading and delivery, where the electrode mounting pad is pre-loaded with one or more therapeutic, anti-inflammatory, and/or pain-relieving drugs prior to the lead being implanted in a patient. Once the electrode mounting pad of the present invention has been secured to a patient's heart, the drugs loaded into the pad are released into the immediately adjacent heart tissue, either instantaneously or at a predetermined controlled rate to thereby inhibit or reduce the occurrence of arrhythmias, reduce pain, inhibit or reduce the occurrence of infections, to effect any combination of the foregoing treatments, and the like. In a preferred embodiment of the present invention, the drug-loaded electrode mounting pad comprises the crosslinked collagen described above.

Examples of anti-arrhythmic drugs suitable for use in loading the biodegradable electrode mounting pad of the present invention include, but are not limited to, Quinidine, Procainamide, Disopyramide (Norpace), Lidocaine (Xylocaine), Mexiletine (Mexitil), Propafenone (Rythmol), Flencainide, beta-adrenergic antagonists, Bretylium (Bretylol), Sotalol (Betapace), Amiodarone (Cordarone), Ibutilide (Corvert), Verpamil (Calan, Isoptin), Diltazem (Cardizem), and Adenosine (Adenocard).

Examples of some non-steroidal anti-inflammatory drugs suitable for use in loading the biodegradable electrode mounting pad of the present invention include, but are not limited to, aspirin, ibuprofen, indomethacin, ketoprofen, meclofenamate, naproxen, phenylbutazone, piroxicam and sulindac. Examples of some steroidal anti-inflammatory drugs suitable for use in loading the biodegradable electrode mounting pad of the present invention include, but are not limited to, beclomethasone, betamethasone, dexamethasone, dexamethasone phosphate, hydrocortisone (cortisol), and prednisone.

Examples of some anti-biotic drugs suitable for use in loading the biodegradable electrode mounting pad of the present invention include, but are not limited to, penicillins (e.g., methicillin, ampicillin, oxacillin), cephalosporins, aminoglycosides (e.g., gentamycin, tobramycin, streptomycin), vancomycin, erythromycin, tetracycline, and chloramphenicol.

Examples of still other types of drugs or substances that may be loaded in the biodegradable electrode pad of the present invention include, but are not limited to, local anesthetics and pain relieving agents, localized gene therapy substances (such as those containing DNA, RNA, viral vectors, and the like), and angiogenic drugs (including growth factors such as vascular endothelial growth factor and fibroblast growth factor).

The biodegradable electrode mounting pad of the present invention may be loaded with a desired drug according to at least six different methods:

(a) placing microspheres in the collagen (or other material) pad, the microspheres containing a predetermined amount of a desired drug and releasing same at a predetermined rate upon contacting the body fluids of a patient;

(b) suspending collagen (or other material) in solution, adding a desired water soluble drug in an appropriate quantity to the solution, freezing or dehydrating the solution, freeze drying the resulting material and forming a collagen (or other material) electrode mounting pad therefrom;

(c) suspending collagen (or other material) in solution, adding a desired non-water-soluble drug in an appropriate quantity to the solution, freezing or dehydrating the solution, freeze drying the collagen (or other material) pad, and forming a collagen (or other material) electrode mounting pad therefrom;

(d) soaking a collagen (or other material) pad in a solution containing a desired drug suspended in solution therein, removing the pad from the solution and drying it, and repeating the soaking and drying steps a sufficient number of times until the desired amount of drug has been imbibed into the electrode mounting pad;

(e) co-valently coupling or bonding the desired drug into the matrix of a collagen (or other material) electrode mounting pad, where the drug has a desired functional group which bonds to a corresponding functional group of the collagen, and (f) placing a paste or cream loaded with the desired drug on and into the matrix of a collagen (or other material) electrode mounting pad, most preferably placing such cream on that side of the collagen (or other material) electrode mounting pad configured to contact the heart.

When the drug-loaded biodegradable electrode mounting pad of the present invention is prepared according to the second preparation method described hereinabove, the water soluble drug loaded into the pad is released as soon as or shortly after coming into contact with the patient's body fluids. As such, the drugs loaded into the pad are released into the body fluids surrounding the site where the electrode mounting pad is secured to the patient's heart. Water soluble drugs may be employed when forming the electrode pad of the present invention to permit release of nearly all the drug contained within the pad to the body fluid of the patient within 24 hours or so of implantation.

Contrariwise, when the drug-loaded collagen (or other material) electrode mounting pad of the present invention is prepared according to the third preparation method described hereinabove, the non-water-soluble drug loaded into the pad may be configured to be released when that portion of the pad within which it resides or is attached to begins to decompose or dissolve in body fluids. In other words, as various portions of the pad dissolve and come into contact with body fluids the drugs contained within those portions are released. Non-water-soluble drugs may be employed to provide relatively prolonged release of the drugs contained within the pad, the release being mediated by cell ingrowth into the pad and biodegradation thereof.

Depending on the particular application at hand, salt or non-salt versions of various drugs may be employed during the drug-loading and electrode preparation steps of the present invention to thereby control the time rate at which the drug is released after the electrode mounting pad is implanted within a patient. When the drug to be loaded into the pad is dissolved in a solvent during the drug loading and pad preparation processes, the solvent may be permitted to merely evaporate after the drug has been placed in solution therein. Media other than water such as alcohol, ether, and solvents may be employed in the drug loading and electrode pad preparation processes of the present invention.

A drug loaded collagen electrode mounting pad of the present invention may be configured and formed such that the outer collagenous surface of the pad not coming into contact with a patient's heart is less permeable to the passage of body fluids therethrough than is the inner collagenous surface of the pad which does come into contact with the patient's heart. In such a configuration of the electrode mounting pad of the present invention, where the collagenous material forming the inner surface of the pad has larger interstices and is less dense than the collagenous material forming the outer surface of the pad (which has smaller interstices and is more dense), drugs loaded into the matrix of the pad are preferentially targeted and directed to the heart wall, thereby reducing the amount of the drug loaded into the pad that might be carried away from the intended treatment site by body fluids to other locations within the body.

It is a further advantage of such an embodiment of the drug loaded collagen electrode mounting pad of the present invention that the more dense outer collagenous surface exhibits less of an affinity for or adhesive characteristic in respect of the pericardial sac; a temporary lead of the present invention is typically implanted such that the electrode mounting pad thereof is located within the pericardial sac such that its outer surface is disposed towards the pericardial sac. It is therapeutically beneficial for the outer surface not to adhere or stick to the pericardium.

Further information and teachings concerning bioerodable materials, biodegradable materials, particular drugs, drug loading and preparation techniques, collagen formation and use techniques, and therapeutic amounts of drugs may be found in one or more of the following issued patents:

U.S. Pat. No. 4,913,903 for "Post-Surgical Applications for Bioerodable Polymers" to Sudman et al.;

U.S. Pat. No. 5,876,452 for "Biodegradable Implant" to Anthanasiou et al.;

U.S. Pat. No. 5,851,229 for "Bioresorbabable Sealants for Porous Vascular Grafts" to Lentz et al.;

U.S. Pat. No. 5,833,651 for "Therapeutic Intraluminal Stents" to Donovan et al.;

U.S. Pat. No. 5,833,665 for "Polyurethane-Biopolymer Composite" to Bootman et al.;

U.S. Pat. No. 5,739,176 for "Biodegradable In-Situ Forming Implants and Methods of Making Same" to Dunn et al.;

U.S. Pat. No. 5,733,950 for "Biodegradable In-Situ Forming Implants and Methods of Producing Same" to Dunn et al.;

U.S. Pat. No. 5,733,563 for "Albumin Based Hydrogel" to Fortier;

U.S. Pat. No. 5,731,005 for "Hydrogel-Based Microsphere Drug Delivery Systems" to Ottoni et al.;

U.S. Pat. No. 5,679,377 for "Protein Microspheres and Methods of Using Them" to Bernstein et al.;

U.S. Pat. No. 5,660,854 for "Drug Rleasing Surgical Implant or Dressing Material" to Haynes et al.;

U.S. Pat. No. 5,660,848 for "Subdermally Implantable Device" to Moo-Yong;

U.S. Pat. No. 5,635,493 for "Methods and Compositions for Poly-Beta-N-Acetylglucosamine Chemotherapeutics" to Vournakis et al.;

U.S. Pat. No. 5,618,563 for "Biodegradable Polymer Matrices for Sustained Delivery of Local Anesthetic Agents" to Berde et al.;

U.S. Pat. No. 5,487,895 for "Method for Forming Controlled Release Polymeric Substrate" to Dapper et al.;

U.S. Pat. No. 5,387,419; U.S. Pat. No. 5,466,233 for "Tack for Intraocular Drug Delivery and Method for Inserting and Removing Same" to Weiner et al.;

U.S. Pat. No. 5,387,419 for "System for Controlled Release of Antiarrhythmic Agents" to Levy et al.;

U.S. Pat. No. 5,340,849 for "Biodgradable In-Situ Forming Implants and Methods for Producing the Same" to Dunn et al.;

U.S. Pat. No. 5,154,182 for "Drug or Steroid Releasing Patch Electrode for an Implantable Arrhythmia Treatment System" to Moaddeb;

U.S. Pat. No. 5,128,326 for "Drug Delivery Systems Based on Hyalurnans Derivatives Thereof and Their Salts and Methods of Producing Same" to Balazs et al.;

U.S. Pat. No. 4,938,763 for "Biodegradable In-Situ Forming Implants and Methods of Producing the Same;"

U.S. Pat. No. 4,913,903 for "Post-Surgical Applications for Bioerodable Polymers" to Sudmann et al.;

U.S. Pat. No. 4,584,188 "Hydrogels" to Graham;

U.S. Pat. No. 4,450,150 for "Biodegradable, Implantable Drug Delivery Depots, and Method for Preparing and Using Same" to Sidman, and U.S. Pat. No. 4,351,337 for "Biodegradable, Implantable Drug Delivery Device, and Process for Preparing and Using Same" to Sidman.

At least some of the materials, devices or processes disclosed in the patents set forth above may be modified advantageously in accordance with the teachings of the present invention.

Figure 11:
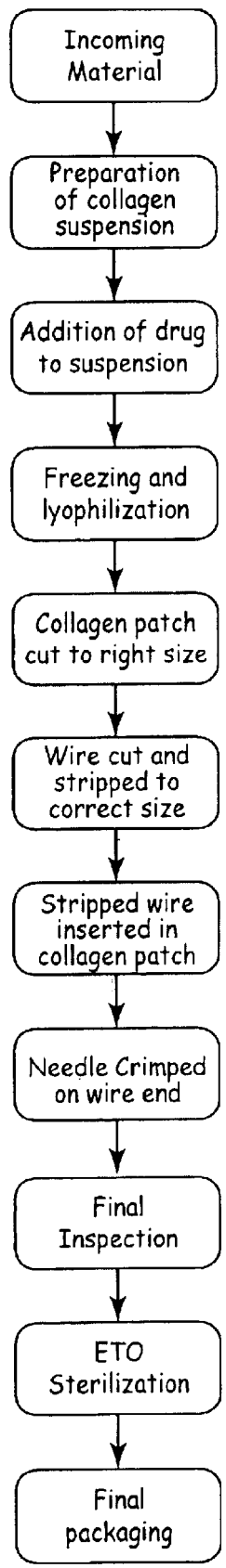
FIG. 11 illustrates one method loading a drug into an electrode mounting pad of the invention.

FIG. 11 is a flow chart for one method of making one embodiment of a drug-loaded biodegradable electrode mounting pad of the present invention. In FIG. 11, the process of making a drug-loaded biodegradable electrode mounting pad begins with obtaining appropriate medical grade collagen. At room temperature one gram of collagen is dissolved in 100 grams of 0.01 M acetic acid solution and slowly agitated to form a collagen suspension solution containing 1 percent by weight collagen. Ten milligrams of amiodarone hydrochloric acid are added to 90 milligrams of ethanol to form 100 mg of a drug solution which is then added to the 90 ml collagen suspension solution. After mixing and agitating the resulting solution, the drug-containing collagen solution is poured into a 6 cm by 6 cm metal cast, and then frozen and freeze-dried using conventional processes. Following freeze-drying, the collagen sponge is pressed for 30 seconds between two plates heated to 80 degrees Celsius and exerting a pressure of 180 bars to produce a collagen pad having a thickness of 3 mm. Thereafter, the pressed collagen pad is cut to appropriate size, and the other components comprising a lead of the present invention are configured and attached as required to the pad in accordance with the teachings disclosed hereinabove.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to the use of any particular specific configuration of temporary defibrillation or pacing lead or electrode shown explicitly in the drawings hereof. The electrode mounting pad of the present invention need not be made of collagen, but may be formed from any other suitable biodegradable, biocompatible material which provides substantially the same function as the collagen electrode mounting pads disclosed explicitly herein. Although crosslinked collagens are preferred for the electrode mounting pad of the present invention, non-crosslinked collagen materials may also be used. Additionally, the stimulating electrode employed in conjunction with the present invention need not be a single wire or a single electrode attached to a single electrical conductor. Those skilled in the art will understand immediately that many variations and permutations of known electrical conductor/stimulating electrode configurations may be employed successfully in the present invention.

The present invention is also not limited to use in conjunction with temporary defibrillation or cardioversion leads, but may also be employed as a temporary pacing lead in bradycardia applications, as a cardiac sensing lead only, as a fetal monitoring and/or sensing lead, a fluoroless lead, a balloon lead, or a lead for use in stent implantation or other surgical procedure where cardiac backup, pacing support or defibrillation is required.

In the claims, means plus function clauses are intended to cover the structures described herein as performing the recited function and their equivalents. Means plus function clauses in the claims are not intended to be limited to structural equivalents only, but are also intended to include structures which function equivalently in the environment of the claimed combination.

All printed publications and patents referenced hereinabove are hereby incorporated by referenced herein, each in its respective entirety.

We claim:

1. A method of making a temporary medical electrical lead for pacing or defibrillating a heart of a patient, the lead comprising a lead body having proximal and distal ends, the lead body comprising at least one electrical conductor having proximal and distal ends, an insulative sheath formed of biocompatible and electrically insulative material, the sheath extending over and covering at least portions of the at least one electrical conductor, an electrical connector assembly attached to the proximal end of the at least one electrical conductor for attachment to a device capable of providing pacing or defibrillation pulses therethrough, and an electrode mounting pad disposed near the distal end of the lead body, at least one of the distal end of the at least one electrical conductor and an electrode member secured to the distal end of the at least one electrical conductor being attached to or integrated into the electrode mounting pad, the electrode mounting pad comprising a biodegradable, biocompatible material soluble in human body fluids, the material forming a matrix having open voids or spaces disposed therein, and a drug for treating a medical condition of the patient's heart, the drug being incorporated in, or disposed on or in at least portions of the matrix, the drug being released to body fluids following implantation of the pad within the patient's body adjacent the heart, the method comprising:

(a) providing the at least one electrical conductor;

(b) providing the insulative sheath;

(c) providing the electrode mounting pad in the form of a cast matrix structure having an outer heart non-contacting surface and an inner heart contacting surface, a collagenous material forming the outer surface of the collagen mounting pad being less permeable to passage of body fluids than a collagenous material forming the inner surface of the collagen mounting pad and wherein the collagenous material of the inner surface of the pad has larger interstices and is less dense than the collagenous material of the outer surface of the pad;

(d) providing the connector assembly;

(e) providing the drug;

(f) loading the drug into the matrix of the pad;

(g) disposing the insulative sheath over the at least portions of the electrical conductor;

(h) attaching the connector assembly to the proximal end of the at least one electrical conductor, and (i) attaching at least portions of the distal end of the at least one electrical conductor or of the electrode member to the electrode mounting pad.

2. The method of claim 1, wherein loading the drug in the pad is accomplished by placing microspheres in the collagen pad, the microspheres containing a predetermined amount of a desired drug and releasing same at a predetermined rate upon contacting the body fluids of the patient.

3. The method of claim 1, wherein loading the drug in the pad is accomplished by suspending collagen in a solution, adding a desired water soluble drug in an appropriate quantity to the solution, dehydrating the solution, freeze drying the resulting material and forming the drug loaded collagen electrode mounting pad therefrom.

4. The method of claim 1, wherein loading the drug in the pad is accomplished by suspending collagen in a solution, adding a desired non-water-soluble drug in an appropriate quantity to the solution, dehydrating the solution, freeze drying the collagen pad, and forming the drug loaded collagen electrode mounting pad therefrom.

5. The method of claim 1, wherein loading the drug in the pad is accomplished by soaking the collagen pad in a solution containing a desired drug suspended in solution therein, removing the pad from the solution and drying it, and repeating the soaking and drying steps a sufficient number of times until a desired amount of drug has been imbibed into the electrode mounting pad.

6. The method of claim 1, wherein loading the drug in the pad is accomplished by co-valently coupling or bonding the desired drug into the matrix of the collagen electrode mounting pad, where the drug has a desired functional grouping which bonds to a corresponding functional grouping of the collagen.

7. The method of claim 1, wherein loading the drug in the pad is accomplished by disposing a paste or cream loaded with the desired drug on and into the matrix of the collagen electrode mounting pad.

8. The method of claim 7, wherein the cream or paste is disposed on a side of collagen electrode mounting pad configured to contact the heart.

9. The method of claim 1, wherein the collagen is crosslinked prior to being attached to the distal end of the at least one electrical conductor.

10. The method of claim 1, wherein the collagen is freeze dried prior to being attached to the distal end of the at least one electrical conductor.

11. The method of claim 1, wherein the collagen ETO-sterilized prior to being attached to the distal end of the at least one electrical conductor.

12. The method of claim 1, wherein providing the drug is preceded by selecting the drug from the group consisting of an anti-arrhythmic drug, an anti-inflammatory drug, an anti-biotic drug, a local anesthetic, and a pain relief agent.

13. The method of claim 1, wherein providing the drug is preceded by selecting the drug from the group consisting of quinidine, procalnamide, disopyramide, lidocaine, mexiletine, propafenone, fiencainide, a beta-adrenergic antagonist, bretyllum, sotalol, amiodarone, ibutilide, verpamil, diltazem, and andenosine.

14. The method of claim 1, wherein providing the drug is preceded by selecting the drug from the group consisting of dexamethazone, dexamethazone phosphate, a steroid, ibuprofen, aspirin, and baclomethazone.

15. The method of claim 1, wherein providing the drug is preceded by selecting the drug from the group consisting of genamyacin, penicillin, methacillin and tertracycline.

* * * * *

UNITED STATES PATENT AND TRADEMARK OFFICE
CERTIFICATE OF CORRECTION

PATENT NO. : 6,748,653 B2
DATED : June 15, 2004
INVENTOR(S) : Frederic W. Lindemans et al.

It is certified that error appears in the above-identified patent and that said Letters Patent is hereby corrected as shown below:

Column 20,
Line 23, delete "procalnamide" and insert -- procainamide --.
Line 25, delete "bretyllum" and insert -- bretylium --.

Signed and Sealed this

Ninth Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,748,653 B2
DATED : June 15, 2004
INVENTOR(S) : Fredric W. Lindemans et al.

It is certified that error appears in the above-identified patent and that said Letters Patent is hereby corrected as shown below:

Title page,
Item [57], ABSTRACT,
Line 17, delete "for treating for treating" and insert -- for treating --.

Column 18,
Line 54, delete "surface, a collagenous material forming the outer surface of the collagen mounting pad being less" and insert -- surface, the outer surface being less --.
Line 56, delete "fluids than a collagenous material forming the inner surface of the collagen mounting pad and wherein the collagenous mateial of the inner surface of the pad has larger interstices and is less dense than the collagenous material of the outer surface of the pad;" and insert -- fluids than a collagenous material forming the inner surface of the collagen mounting pad and wherein the collagenous material of the inner surface of the pad has larger interstices and is less dense than the collagenous material of the outer surface; --.

Column 20,
Lines 8, 11 and 14, delete "wherein the" and insert -- wherein a --.

Signed and Sealed this

Nineteenth Day of July, 2005

JON W. DUDAS
*Director of the United States Patent and Trademark Office*